United States Patent [19]

Masaichiro

[11] Patent Number: 4,564,475
[45] Date of Patent: Jan. 14, 1986

[54] COMPOSITIONS CONTAINING UNSATURATED FATTY ACID COMPOUNDS AND METHOD OF STABILIZING UNSATURATED FATTY ACID COMPOUNDS

[75] Inventor: Masui Masaichiro, Takarazuka, Japan

[73] Assignees: Hiroshi Sekimoto, Ishikawa; Michio Nakanishi, Osaka; Masataka Akiyoshi, Hyogo, all of Japan

[21] Appl. No.: 615,095

[22] Filed: May 29, 1984

[30] Foreign Application Priority Data

May 28, 1983 [JP] Japan .................................. 58-94489
Jul. 2, 1983 [JP] Japan ................................ 58-120693

[51] Int. Cl.$^4$ .............................................. A23J 7/00
[52] U.S. Cl. .................................. 260/398.5; 260/403; 260/925; 260/945; 252/403; 252/400 R
[58] Field of Search ...................... 260/403, 398.5, 925, 260/945; 252/400.2, 400.21, 403

[56] References Cited

U.S. PATENT DOCUMENTS 3,632,627 1/1972 Gordon et al. ...................... 260/945
4,129,650 12/1978 Betzing et al. ...................... 260/403

OTHER PUBLICATIONS

Kirk Othmer Encyclopedia of Chemical Technology, 2nd Edition, John Wiley & Sons, Inc., 1965, p. 781.

*Primary Examiner*—Anton H. Sutto
*Assistant Examiner*—Elizabeth A. Flaherty
*Attorney, Agent, or Firm*—Wenderoth, Lind & Ponack

[57] ABSTRACT

This invention relates to a stable composition containing a unsaturated fatty acid having 20 to 22 carbon atoms and 3 or more double bonds, and a method of stabilizing such fatty acid compounds by using as the stabilizing agent, at least one species of the compounds represented by the following general formula:

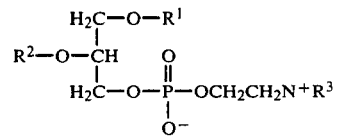

wherein $R^1$ and $R^2$ respectively stand for a fatty acid residue, and $R^3$ stands for $(H)_3$ or $(CH_3)_3$.

7 Claims, No Drawings

COMPOSITIONS CONTAINING UNSATURATED FATTY ACID COMPOUNDS AND METHOD OF STABILIZING UNSATURATED FATTY ACID COMPOUNDS

FIELD OF THE INVENTION

This invention relates to a stable composition containing an unsaturated fatty acid having 20 to 22 carbon atoms and 3 or more (usually 3 to 6) double bonds and derivatives thereof (hereafter referred to as fatty acid compounds A) and a method of stabilizing fatty acid compounds A.

BACKGROUND OF THE INVENTION

Compounds belonging to fatty acid compounds A can be exemplified by:

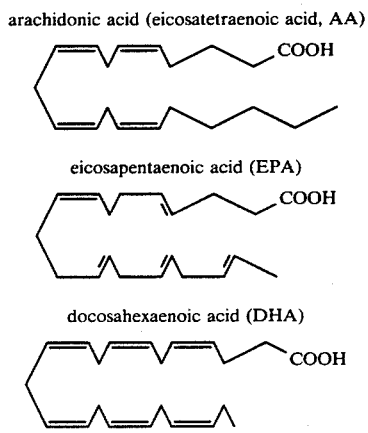

arachidonic acid (eicosatetraenoic acid, AA)

eicosapentaenoic acid (EPA)

docosahexaenoic acid (DHA)

These AA, EPA and DHA are important substances acting as precursors of a group called respectively prostaglandine (PG), thromboxane and leucotriene. These latter substances are possessed of respectively characteristic strong physiological activities and, PG, for example, has a blood-platelet-agglutination-inhibitory-action and contracting and dilating action against arterial wall, and thus can be expected to be useful in prevention of thrombosis and arteriosclerosis, and can also be expected to exhibit anti-cancer action. However, former substances cannot be produced in the human body and, therefore, must be supplied from outside the body. These substances are contained largely in marine products, especially in sardines or mackerels. Therefore, said unsaturated fatty acid is extracted from these fishes as sardine oil and mackerel oil, and can be used, as they are or in a form of amide, ester such as alkylester (e.g. ethylester) triglyceride and the like, as medicines or health-aid foods.

On the other hand, these fatty acid compounds A have many unsaturated bonds and poor stability, thus being readily deteriorated in a relatively short period of time. Fishes are often frozen or dried as they are or made into processed foods (e.g. dried bonito or fishes dried whole). Sometimes, EPA or DHA or the like is extracted from fish oil as it is or in a form of ester, which is then refined. Even in this sort of processing, the unstability of fatty acid compounds A is a problem. Besides, fishes or components of fish oils, when processed or stored for a long period of time, produce rusting.

Under the circumstances, the present inventor has made an extensive study and found that a compound represented by the general formula (I):

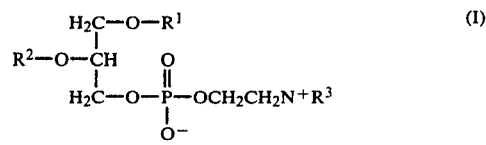

(wherein $R^1$ and $R^2$ respectively stand for fatty acid residue, and $R^3$ stands for $(H)_3$ or $(CH_3)_3$) [hereinafter called Compound (I)] has an action or stabilizing fatty acid compounds A, thus completing this invention.

SUMMARY OF THE INVENTION

An object of this invention lies in providing a stable composition containing a fatty acid compound A.

Another object is to provide a method of stabilizing fatty acid compounds A.

Still another object is to provide a method of stabilizing fish and fish oil.

Further object lies in providing a method of improving stability in processing fish and fish oil.

This invention relates to a stable composition containing fatty acid compounds A, which is incorporated with, as a stabilizing agent, at least one species of the compounds (I), a method of stabilizing fatty acid compounds A, which is characterized by incorporating at least one species selected from compounds (I) into fatty acid compounds A or a composition containing them, and, a method of stabilizing fish or fish oil, characterized by allowing at least one species selected from compounds (I) to be present in the step of processing fish and fish oil.

DETAILED DESCRIPTION OF THE INVENTION

In the present invention, fatty acid compounds A mean unsaturated fatty acids having 20 to 22 carbon atoms and 3 or more (usually 3 to 6) double bonds as well as their derivatives, especially those at the carboxyl group (e.g. esters such as alkylester, triglyceride, etc., and amides, etc.). As the alkyl in the above-mentioned alkylester, there may be exemplified 1-4C lower alkyl such as methyl, ethyl, n-propyl, isopropyl, n-butyl, iso-butyl, t-butyl, etc.

The fatty acid compounds A may for example be AA, EPA, DHA, EPA triglyceride, DHA triglyceride, EPA ethylester.

The compound (I) is incorporated into the above-mentioned fatty acid compounds A per se and substances containing them. As the substances containing fatty acid compounds A, there may be exemplified sardine oil, mackerel oil, etc., or compositions containing fatty acid compounds A incorporated with a carrier which is usually employed for medicines, health-aid foods, etc.

The processing of fish or fish oil in the present invention means subjecting fish or components of fish to treatment, for example, heating, freezing, drying, etc., which may be exemplified by preparation of dried fish such as dried bonito, sardines dried whole, dried horse mackerel, preparation of smoked fish, production and purification of fish oil, etc.

The fatty acid residue represented by $R^1$ and $R^2$ in the general formula (I) is an ester-linkage fatty acid (i.e.

acyl group), which may be straight-chained or branched and saturated or unsaturated, whose carbon number is preferably within the range of 2–30. $R^1$ and $R^2$ may be the same as or different from each other.

As $R^1$ and $R^2$ are exemplified residues of fatty acids such as propionic acid, capric acid, stearic acid, palmitic acid, oleic acid, linoleic acid, etc.

Compounds (I) may be exemplified by phosphatidyl choline, phosphatidyl ethanolamine, lysophosphatidyl choline, inositol phosphatide, etc. Compounds (I) may be incorporated into compositions of this invention also as a suitable mixture. When incorporated as a mixture, it is preferably as lecithin. As lecithin, that present in natural sources, i.e. animals and vegetables may be used as it is or after refining, for example, yolk lecithin, soybean lecithin, etc. may be mentioned as preferable ones.

The amount of compound (I) to be incorporated is preferably 0.5 weight % or more, more preferably 1 weight % or more, most preferably 10% or more relative to fatty acid compounds A.

The composition of this invention is more preferably in a powdery form supplemented with cyclodextrin, which serves to remarkably minimize unpleasant odor and bitterness peculiar to fatty acid compounds A, and also serves to make the composition pleasant to the tongue.

The cyclodextrin-containing powdery preparation can be prepared by the following method.

First, compound (I), for example lecithins, are dissolved in fatty acid compounds A under heating. The heating temperature is that which will dissolve the fatty acid compounds A and compound (I). To thus-obtained oily matter is added cyclodextrin under stirring, followed by cooling to yield the intended powdery product. The amount of cyclodextrin to be added is usually more than that of the fatty acid compounds A, preferably more than three times as much in terms of weight. The cyclodextrin to be added may be any of $\alpha$-, $\beta$- or $\gamma$-isomer, or may a mixture thereof, or may be a mixture with dextrin.

Into the composition of this invention may be further incorporated vitamin A, vitamin C or vitamin E as stabilizers.

The composition of this invention may be used as it is, or may be administered in a form of tablet, capsule, granule, etc. by using conventional carriers or the like.

The present invention will be explained more concretely by way of the following examples, but they are not intended to limit the invention in any manner whatsoever.

EXAMPLE 1

Two grams each of the fatty acid compounds A listed in the column of "Samples" of Table 1 was taken into test tubes. To each of the test tubes was added each of the stabilizing agents listed in the column of "Stabilizing Agents" in the respective weight % shown in Table 1. The respective contents were well mixed. Thus-obtained compositions in the test tubes were left standing uncapped on a thermostat waterbath at 70° C.

Using these samples, remaining ratios of fatty acid compounds A contained therein were determined at 24 hours, 48 hours and six days after addition of the stabilizing agents, relative to the amount of fatty acid compounds A at the initial stage as 100%. The results are shown in Table 1.

Method of Quantitative Determination:

To 100 mg each of the sample compositions was added methanol solution containing 1% caustic soda to make a 1 ml solution. Thus-prepared sample solutions were vigorously shaken while heating. Each of the complete solutions was subjected to gas-chromatography to determine quantitatively the fatty acid compounds A as its methylester.

Conditions for Quantitative Determination:

5% FFAP on Uniport B/2 m
Glass column
Column temperature: 205° C.

The composition to which no stabilizing agent was added increased its viscosity gradually, and 6–7 days later, gellation on the surface was observed, while no change was observed on the sample composition to which Compound (I) was added.

EXAMPLE 2

Sardine oil was dissolved in ten times as much volume of a mixed solution of ethyl alcohol and concentrated sulfuric acid. The solution was stirred at 50° C. for 30 hours, followed by neutralization of sulfuric acid by sodium carbonate. To the solution was added soybean lecithin in an amount of 5 weight % relative to the sardine oil. The mixture was subjected to distillation in vacuo to prepare EPA-ethylester. The yield was about 50% higher than the case where soybean lecithin was not used.

EXAMPLE 3

To 20 g of EPA oil (containing 25% of EPA triglyceride and 13% of DHA triglyceride) was added 10 g of soybean lecithin. The mixture was dissolved by heating at 40° C. To the solution was added 70 g of cyclodextrin. The mixture was stirred, followed by cooling to yield a yellowish dry powder of EPA oil (A). This (A) and an EPA oil powder prepared without addition of soybean lecithin (B) were left standing for 30 hours on a thermostat bath of 37° C. with putting each of them in an uncapped vessel. The respective EPA contents were determined to find that 80% of EPA remined in (A) while 16% of EPA remained in (B). (A) is remarkably minimized in unpleasant odor and bitterness peculiar to EPA oil.

TABLE 1

| | | Sample | | | | | | | |
|---|---|---|---|---|---|---|---|---|---|
| | | AA | | EPA Triglyceride | | Mixture of each Triglyceride of EPA and DHA (2:1) | | | EPA Ethylester (Purity: 60%) |
| Stabilizing Agent | | 24 hrs. | 48 hrs. | 24 hrs. | 48 hrs. | 24 hrs. | 48 hrs. | 6 days | 24 hrs. | 48 hrs. |
| | | Residual Ratio (%) of Fatty Acid Compounds A | | | | | | | | |
| Egg-yolk lecithin | 30% | —** | 105 | — | 107 | 98 | 95 | — | — | — |
| | 20% | — | 98 | — | 98 | — | — | — | — | — |
| | 10% | — | 100 | — | 95 | — | — | — | — | — |
| Soybean lecithin | 30% | — | — | 98 | 95 | — | — | — | — | — |
| | 20% | — | — | 94 | 91 | — | — | — | — | — |
| | 10% | — | — | 88 | 85 | — | — | — | — | — |

TABLE 1-continued

| Stabilizing Agent | | AA 24 hrs. | AA 48 hrs. | EPA Triglyceride 24 hrs. | EPA Triglyceride 48 hrs. | Mixture of each Triglyceride of EPA and DHA (2:1) 24 hrs. | 48 hrs. | 6 days | EPA Ethylester (Purity: 60%) 24 hrs. | 48 hrs. |
|---|---|---|---|---|---|---|---|---|---|---|
| General formula (I) | 30% | — | — | — | — | — | — | — | — | — |
| $R^1$, $R^2$: | 20% | — | — | 93 | 91 | 90 | 91 | — | — | — |
| Palmitic acid residue | 10% | — | — | — | — | — | — | — | — | — |
| General formula (I) | 30% | — | — | 90 | 88 | 88 | 83 | — | — | — |
| $R^1$: Propionic acid residue | 20% | — | — | — | — | — | — | — | — | — |
| $R^2$: Oleic acid residue | 10% | — | — | — | — | — | — | — | — | — |
| Phosphatidyl ethanol amine | 30% | — | 105 | — | — | 98 | 95 | — | — | 107 |
|  | 20% | — | 98 | — | — | — | — | 75 | — | 98 |
|  | 10% | — | 100 | — | — | — | — | 73 | — | 95 |
| Mixture of phosphatidyl choline and phosphatidyl ethanol amine (ca. 3:2) | 30% | — | — | — | — | — | — | — | — | — |
|  | 20% | — | — | — | — | 93 | 90 | 72 | — | — |
|  | 10% | — | — | — | — | 89 | 90 | 70 | — | — |
| Hydrogenated lecithin* | 10% | — | — | — | — | — | — | — | 98 | 96 |
|  | 5% | — | — | — | — | — | — | — | 92 | 93 |
|  | 1% | — | — | — | — | — | — | — | 96 | 95 |
| Residual Ratio (%) of Eicosapolyenoic Acid Compounds | | | | | | | | | | |
| Vitamin E | 30% | — | — | — | — | 64 | 52 | 15 | — | — |
| Control |  | 83 | 81 | 72 | 65 | 70 | 63 | 27 | 72 | 65 |

*EPIKRON 200SH ® (Q.P. Corporation): Purity >99%
**Dash (—) mean that these values have not been determined.

What is claimed is:

1. A stable composition containing at least one fatty acid compound selected from the group consisting of an unsaturated fatty acid having 20 to 22 carbon atoms and 3 or more double bonds, an amide thereof and an ester thereof, and as a stabilizing agent for the fatty acid compound, at least one compound of the formula:

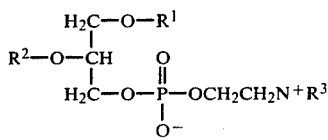

wherein $R^1$ and $R^2$ respectively stand for a fatty acid residue, and $R^3$ stands for $(H)_3$ or $(CH_3)_3$.

2. The composition claimed in claim 1, wherein the compound (I) is incorporated in the composition as lecithin.

3. The composition as claimed in claim 1, wherein the fatty acid compound is incorporated in the composition as fish oil or fish.

4. The composition claimed in claim 1, which further contains cyclodextrin.

5. The composition claimed in claim 2, which further contains cyclodextrin.

6. A method of stabilizing a fatty acid compound selected from the group consisting of an unsaturated fatty acid having 20 to 22 carbon atoms and 3 or more double bonds, an amide thereof and an ester thereof, or a substance containing the fatty acid compound, which comprises incorporating in the fatty acid compound or substance containing the fatty acid compound at least one compound of the formula:

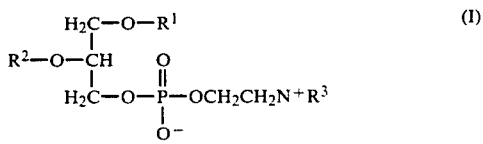

wherein $R^1$ and $R^2$ respectively stand for a fatty acid residue, and $R^3$ stands for $(H)_3$ or $(CH_3)_3$.

7. A method as claimed in claim 6, wherein the compound (I) is incorporated as lecithin.

* * * * *